(12) United States Patent
Kawashima (10) Patent No.: US 10,384,300 B2
(45) Date of Patent: Aug. 20, 2019

(54) METHOD OF MANUFACTURING AN IMMUNOCHROMATOGRAPHIC KIT

(71) Applicant: FUJIFILM Corporation, Tokyo (JP)

(72) Inventor: Takeaki Kawashima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/008,046

(22) Filed: Jun. 14, 2018

(65) Prior Publication Data

US 2018/0290230 A1 Oct. 11, 2018

Related U.S. Application Data

(63) Continuation of application No. PCT/JP2016/005150, filed on Dec. 16, 2016.

(30) Foreign Application Priority Data

Dec. 18, 2015 (JP) ................. 2015-247352

(51) Int. Cl.
  *B32B 37/00* (2006.01)
  *B23K 20/10* (2006.01)
  (Continued)

(52) U.S. Cl.
  CPC .............. *B23K 20/10* (2013.01); *B29C 65/08* (2013.01); *B29C 65/7841* (2013.01);
  (Continued)

(58) Field of Classification Search
  CPC ..... B23K 20/10; B29C 65/08; B29C 65/7841; B29C 66/12441; B29C 66/24244;
  (Continued)

(56) References Cited

U.S. PATENT DOCUMENTS 5,360,499 A * 11/1994 Savovic .................. B29C 65/08
  156/73.1
5,411,616 A * 5/1995 Desai ...................... B29C 65/08
  156/580.1
(Continued)

FOREIGN PATENT DOCUMENTS

JP S5948815 3/1984
JP S64087329 3/1989
(Continued)

OTHER PUBLICATIONS

"International Search Report (Form PCT/ISA/210)"of PCT/JP2016/005150, dated Mar. 14, 2017, with English translation thereof, pp. 1-5.

(Continued)

*Primary Examiner* — James D Sells
(74) *Attorney, Agent, or Firm* — JCIPRNET (57) ABSTRACT

In the ultrasonic welding method, ultrasonic vibration is imparted to a first resin member via a horn while applying a pressing force to the first resin member and a second resin member in which weld portions and come into contact with each other by using a jig for supporting the second resin member and the horn that is disposed to face the jig and in contact with the first resin member so as to weld the first resin member and the second resin member, in which a jig of which a support surface for supporting the second resin member is formed of an elastomer is used as the jig.

14 Claims, 4 Drawing Sheets

(51) Int. Cl.
| | |
|---|---|
| *B29C 65/08* | (2006.01) |
| *B65B 51/22* | (2006.01) |
| *G01N 33/48* | (2006.01) |
| *G01N 33/543* | (2006.01) |
| *G01N 33/558* | (2006.01) |
| *B29C 65/78* | (2006.01) |
| *B29C 65/00* | (2006.01) |
| *B29L 31/00* | (2006.01) |

(52) U.S. Cl.
CPC .. *B29C 66/12441* (2013.01); *B29C 66/24244* (2013.01); *B29C 66/30223* (2013.01); *B29C 66/54* (2013.01); *B29C 66/73921* (2013.01); *B29C 66/8122* (2013.01); *B29C 66/81457* (2013.01); *B29C 66/8322* (2013.01); *B65B 51/22* (2013.01); *G01N 33/48* (2013.01); *G01N 33/543* (2013.01); *G01N 33/558* (2013.01); *B29C 66/543* (2013.01); *B29C 66/71* (2013.01); *B29C 66/81264* (2013.01); *B29C 66/929* (2013.01); *B29L 2031/712* (2013.01)

(58) Field of Classification Search
CPC .............. B29C 66/30223; B29C 66/54; B29C 66/73921; B29C 66/8122; B29C 66/81457; B29C 66/8322; B65B 51/22; G01N 33/48; G01N 33/543; G01N 33/55
USPC ........................................................ 156/73.1
See application file for complete search history.

(56) References Cited

U.S. PATENT DOCUMENTS 5,520,775 A * 5/1996 Fischl ..................... B29C 65/08
  156/580.1
2002/0100535 A1 8/2002 Yamazaki et al.

FOREIGN PATENT DOCUMENTS

| JP | H08-118473 | 5/1996 |
|---|---|---|
| JP | H10-296460 | 11/1998 |
| JP | 2002-301768 | 10/2002 |
| JP | 2006-240293 | 9/2006 |
| JP | 2009-229342 | 10/2009 |
| JP | 2011-99724 | 5/2011 |
| JP | 2012-66546 | 4/2012 |
| WO | 2011111108 | 9/2011 |

OTHER PUBLICATIONS

"Written Opinion of the International Searching Authority (Form PCT/ISA/237)" of PCT/JP2016/005150, dated Mar. 14, 2017, with English translation thereof, pp. 1-16.

"International Preliminary Report on Patentability (Form PCT/IPEA/409) of PCT/JP2016/005150", dated Dec. 12, 2017, with English translation thereof, pp. 1-14.

* cited by examiner

METHOD OF MANUFACTURING AN IMMUNOCHROMATOGRAPHIC KIT

CROSS-REFERENCE TO RELATED APPLICATIONS

This application is a continuation application of International Application No.PCT/JP2016/005150 filed Dec. 16, 2016, which was published under PCT Article 21(2) in Japanese, and which claims priority under 35 U.S.C. § 119(a) to Japanese Patent Application No. 2015-247352, filed Dec. 18, 2015. The above applications are hereby expressly incorporated by reference, in their entirety, into the present application.

BACKGROUND OF THE INVENTION

1. Field of the Invention

The present invention relates to an ultrasonic welding method for a resin container such as an immunochromatographic kit. In addition, the present invention relates to a method for manufacturing a resin container using the ultrasonic welding method.

2. Description of the Related Art

Among immunoassay methods, an immunochromatographic method is easy to operate and is capable of performing measurement within a short period of time and thus is widely generally used as a simple method for detecting test substances.

Specimens in immunochromatographic methods are nasal discharge, saliva, sputum, tears, and the like collected from a patient's nose, throat, conjunctiva, and the like by using an equipment such as gauze or swabs. The specimen is immersed into an extract to disperse or dissolve the specimen so as to prepare a developing solution for immunochromatography measurement, and the measurement is performed by spreading the solution in an immunochromatographic carrier. Generally, the immunochromatographic carrier is accommodated in a casing including an upper case and a lower case, and it is possible to add the developing solution dropwise from a hole for dropwise addition of specimen liquid (developing solution) provided in the casing.

The upper case and the lower case are joined together in state of accommodating the immunochromatographic carrier therein. Examples of the joining method include joining by fitting, joining by heat sealing, joining with an adhesive, joining by ultrasonic welding, and the like (refer to paragraph [0013] of JP2009-229342A).

Meanwhile, in the immunochromatographic method, a technique for amplifying a detection signal has been proposed in order to avoid a problem of showing a false negative because a test substance is not detected due to low sensitivity despite the test substance being contained. JP2011-99724A discloses a method for amplifying by causing a solution including silver ions and a solution including a silver ion reducing agent to react with labels made of metal colloids, metal sulfides, or the like.

SUMMARY OF THE INVENTION

On the other hand, JP2011-99724A discloses an immunochromatographic kit (device) including two types of reagent solutions in a case, but the kit is configured such that supply of a reagent solution is performed in a state where the device is set in a dedicated analyzer. A defect in which the analyzer cannot be used in a situation where electric infrastructures stop, such as disaster, or in an environment where electricity is not working, occurs. Therefore, an immunochromatographic kit that enables manual supply of a reagent solution has been studied, and studies such as incorporating a mechanism for supplying the reagent solution to the case itself have been conducted.

In a case where it is presumed that the reagent solution is supplied manually, it is necessary to sufficiently enhance the airtightness of the container so that the reagent solution does not flow out to the outside of the kit.

However, in JP2011-99724A, since the upper case and the lower case are fitted to each other by fitting portions, there is a case in which the both cases are not in a sealed state.

From the demands of medical cost reduction in recent years, inexpensive and highly versatile inspection devices have been required, and in manufacturing such inspection devices, ultrasonic welding is utilized as an inexpensive joining method that does not require materials such as adhesives and the like for joining resin members as a container.

However, as a result of studies by the present inventors, it became clear that in a case where the ultrasonic welding method is applied for joining the resin members such as the upper and lower cases of the above-described immunochromatographic kit, adhesion defects may occur.

The present invention has been made in view of the above circumstances, and an object thereof is to provide an ultrasonic welding method capable of precisely joining resin members and a method for manufacturing a resin container using the ultrasonic welding method.

According to the present invention, there is provided an ultrasonic welding method for welding a first resin member and a second resin member, the method comprising: imparting ultrasonic vibration to the first resin member via a horn while applying a pressing force to the first resin member and the second resin member in which weld portions come into contact with each other by using a jig for supporting the second resin member and the horn that is disposed to face the jig and in contact with the first resin member so as to weld the first resin member and the second resin member, in which a jig of which a support surface for supporting the second resin member is an elastomer is used as the jig.

The elastomer refers to a substance that deforms in accordance with an imparted force and returns to the original state in a case where the force is removed, and in particular, refers to a substance made of a material having rubber elasticity. The rubber elasticity refers to rubber elasticity of a substance in which modulus of elasticity is smaller than that of a metal, an amount of displacement with respect to force is large, and the modulus of elasticity is about several MPa to several hundred MPa, specifically, about 1 MPa to 60 MPa.

In the ultrasonic welding method of the present invention, the jig is preferably made of a metal body and the elastomer.

A Shore A hardness of the elastomer is preferably A20 to A80.

The elastomer is preferably made of silicone rubber, nitrile rubber, or butadiene rubber.

In the ultrasonic welding method of the present invention, the pressing force is preferably 100 kPa to 300 kPa.

The ultrasonic welding method of the present invention is applied for joining the first resin member and the second resin member which are made of an olefin resin and is particularly suitable in a case where the first resin member is made of an olefin resin containing a softening agent.

According to the present invention, there is further provided a method for manufacturing a resin container followed by joining a first resin member and a second resin member, the method comprising: using the ultrasonic welding method according to the present invention as a method for joining the first resin member and the second resin member.

The method for manufacturing a resin container of the present invention is suitable in a case where the resin container is a housing case that includes an immunochromatographic carrier.

According to the ultrasonic welding method of the present invention, since the jig having the support surface made of the elastomer is used as a jig for supporting the resin members which are adherends, it is possible to join the resin members with high accuracy. Particularly, it is possible to join, with good adhesion, a resin member having a welding length exceeding a total length of 40 mm, or a resin member having high flexibility, which has been difficult to be subjected to the ultrasonic welding in the related art.

DESCRIPTION OF THE PREFERRED EMBODIMENTS

Hereinafter, an embodiment of the present invention will be described using the accompanying drawings, but the present invention is not limited thereto. Meanwhile, in order for better visibility, the reduction scales and the like of individual constitutional elements in the drawings are appropriately changed from actual sizes.

Figure 1:
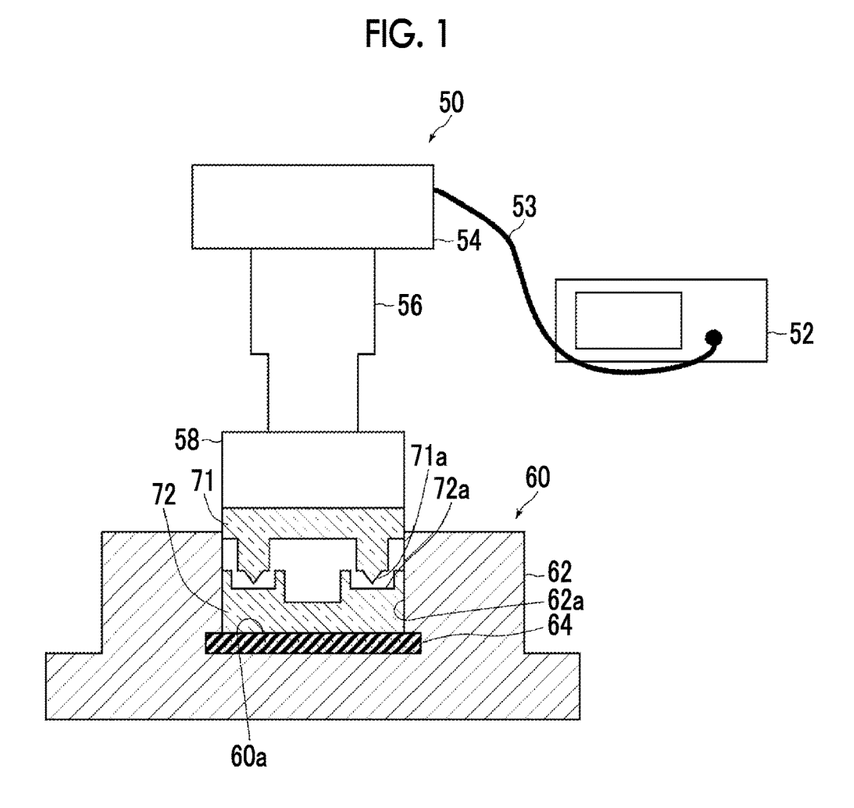
FIG. 1 is a diagram illustrating a schematic configuration of an ultrasonic welding device for carrying out a welding method of an embodiment.

FIG. 1 is a diagram illustrating a schematic configuration of an ultrasonic welding device used for carrying out an ultrasonic welding method of an embodiment.

An ultrasonic welding device 50 includes an ultrasonic oscillator 52, an ultrasonic oscillator 54, a converter 56, a horn 58, and a pressing mechanism not shown.

The ultrasonic oscillator 52 internally converts an electric signal of 50/60 Hz input from the outside into an electric signal of ultrasonic wave (frequency of about 20 kH or higher).

The ultrasonic oscillator 54 is connected to the ultrasonic oscillator 52 by a connection cable 53, and the electric signal generated by the ultrasonic oscillator 52 is transmitted to the ultrasonic oscillator 54. The ultrasonic oscillator 54 converts a signal from the ultrasonic oscillator 52 into vibration energy. The ultrasonic oscillator 54 converts the electric signal from the ultrasonic oscillator 52 into vibration energy so as to vibrate, and this mechanical vibration is transmitted to the converter 56.

The converter 56 has a booster function, and the vibration transmitted from the ultrasonic oscillator 54 is first amplified in the converter 56 so that the amplitude is adjusted, and then is transmitted to the horn 58.

The horn 58 has a function of sandwiching a welding object to be described later, with a jig to be described later and transmitting ultrasonic vibrations to the welding object.

Figure 2:
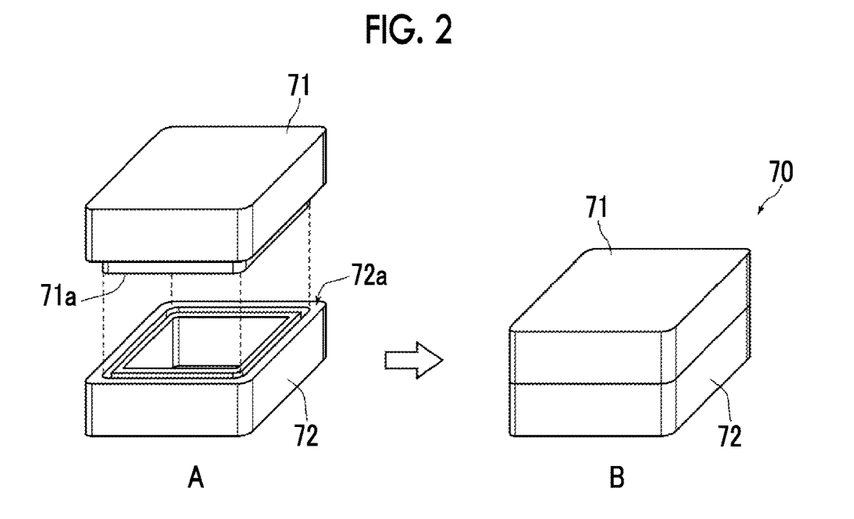
FIG. 2 is a perspective view illustrating a resin container before and after welding.

An ultrasonic welding method according to an embodiment of the present invention using the ultrasonic welding device 50 will be described. FIG. 2 is a perspective view schematically illustrating an example of the welding object before welding (A) and after welding (B), which is joined by the welding method of the present embodiment. Hereinafter, a case in which a first resin member 71 and a second resin member 72 shown in A of FIG. 2 are joined to each other at a weld portion 71a of the first resin member 71 and a weld portion 72a of the second resin member 72 so as to produce a resin container 70 shown in B of FIG. 2, will be explained.

Figure 3:
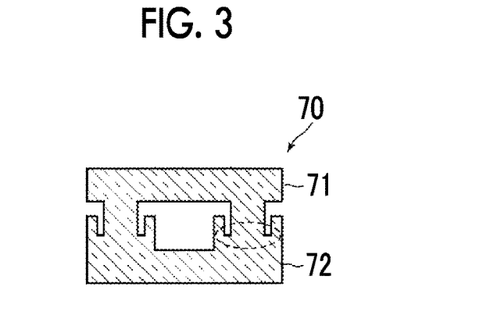
FIG. 3 is a schematic sectional view of the resin container after welding.

First, a jig 60 for supporting one (the second resin member 72) of the two welding (joining) objects (the first resin member 71 and the second resin member 72) is prepared. As the jig 60, a jig including a main body 62 having a concave portion 62a for receiving the second resin member 72, and an elastomer 64 disposed on a bottom surface of the concave portion 62a, that is, a jig in which a support surface 60a in contact with a bottom surface of the second resin member 72 is formed by the elastomer 64, is used. The support surface 60a is a surface substantially perpendicular to a direction of pressing applied at the time of welding. In regard to the first resin member 71, the second resin member 72 which are the adherends disposed below the horn 58, and the jig 60 in FIG. 1, cross sections thereof are shown. In addition, in regard to the first and second resin members 71 and 72, enlarged weld portions 71a and 72a thereof are shown. FIG. 3 is a schematic cross-sectional view of the resin container 70 formed by welding the first and second resin members 71 and 72.

The main body 62 of the jig 60 is preferably made of a metal such as stainless steel. In a case where a wall surface other than the bottom surface of the concave portion 62a is made of a material having a high level of stiffness such as metal, the resin member supported at the time of ultrasonic welding does not cause positional deviation in a planar direction (direction parallel to the bottom surface), which is preferable.

As the elastomer 64 constituting the support surface 60a of the jig 60, it is preferable to use rubber, and both natural rubber and synthetic rubber can be used, but synthetic rubber is preferable, among which silicone rubber, nitrile rubber, or butadiene rubber is more preferable, and silicone rubber is particularly preferable.

A hardness of the elastomer can be expressed by a modulus of elasticity or a Shore A hardness. It is assumed that the elastomer has a modulus of elasticity (Young's modulus) of 1 MPa to 60 MPa, but 1 MPa to 45 MPa is particularly preferable. A Shore A hardness is a general index representing a hardness of rubber and is a numerical value obtained by pressing an indenter against a surface of a non-measurement object by using a durometer and measuring an indentation depth thereof. In the present invention, the elastomer preferably has a Shore A hardness of A20 to A80, particularly more preferably A40 to A60, and still more preferably A50.

The Young's modulus of the elastomer is a value measured according to ISO 527, and the Shore A hardness is a value measured according to ISO 23529.

A thickness of the elastomer is preferably 0.4 mm to 3.0 mm and more preferably 0.5 mm to 2.5 mm because the elastomer has high durability and more uniform ultrasonic welding is possible.

The first resin member 71 and the second resin member 72 are set between the horn 58 and the jig 60 in a state where the weld portions 71a and 72a are brought into contact with each other in advance. At the time of welding, the horn 58 comes in contact with the first resin member 71 so as to impart ultrasonic vibration thereto while the horn 58 imparts pressing force against the first and second resin members 71 and 72 from the first resin member 71 side by a pressing mechanism. Accordingly, vibration is converted into thermal energy at the weld portions 71a and 72a, which are in contact with each other, of the first and second resin members 71 and 72, and the resin is melted, and therefore the resin members 71 and 72 are bonded to each other at the weld portion indicated by a broken line in FIG. 3.

According to the ultrasonic welding method of the present embodiment, by using the jig in which the support surface for supporting the second resin member is formed by the elastomer, it is presumed that vibration due to ultrasonic waves is uniformly transmitted because uniform sealed state of the first resin member on an upper part and the second resin member on a lower part is realized, and therefore it is possible to perform favorable welding between resin members.

It is preferable that the weld portion 71a of the first resin member 71 disposed on the horn 58 side among the first resin member 71 and the second resin member 72, is a protrusion portion so that melting by concentration of ultrasonic waves easily occur. The weld portion 71a formed of a protrusion portion comes into contact with the weld portion (joining surface) 72a of which a distal end becomes a joining target and is melted and adheres to the weld portion 72a by ultrasonic vibration. A cross-sectional shape of the protrusion portion is preferably a pointed tip, typically triangular, so that ultrasonic vibration concentrates at the distal end thereof.

The ultrasonic welding method of the present invention can be applied to adhesion of any resin member to each other, but particularly is suitable for a case in which at least one of the resin member of the two objects to be welded to each other, has flexibility to the extent that the resin member can be deformed by being pressed by a finger of a human or the like.

A material having flexibility suitable for the ultrasonic welding method of the present invention is a resin having an elongation at break of 100% to 1000%. For example, by using polypropylene or low-density polyethylene, a resin component exhibiting such elongation at break can be molded. The elongation at break (tensile elongation) is an elongation percentage with respect to the original length in a case where a test piece is stretched until fractured and is measured by a method conforming to the ISO 37 standard.

A pressure applied to the weld object at the time of ultrasonic welding may be appropriately determined according to a material and a shape of the weld object, but in a case of welding the resin member having flexibility described above, the pressure is preferably 100 kPa or more, preferably about 300 kPa.

A method for manufacturing a resin container of the present invention includes a step of joining the first resin member and the second resin member by the above welding method.

The resin constituting the resin container is appropriately selected according to the use of the resin container, from the viewpoint of flexibility, moldability, heat resistance, chemical resistance, and the like. Specific examples of the resin material include polystyrene, polyethylene, polyvinyl chloride, polypropylene, polycarbonate, polyester, polymethyl methacrylate, polyvinyl acetate, vinyl-acetate copolymer, styrene-methyl methacrylate copolymer, acrylonitrile-styrene copolymer, acrylonitrile-butadiene-styrene copolymer, nylon, polymethylpentene, silicon resin, amino resin, polysulfone, polyether sulfone, polyether imide, fluororesin, polyimide, and the like. Among these resins, from the viewpoint of flexibility, moldability, and the like, an olefin resin is preferable, among which polyethylene, polypropylene, and polyvinyl chloride are preferable, and polypropylene is particularly preferable.

Hereinafter, a method for manufacturing an immunochromatographic kit will be described as an embodiment of the method for manufacturing a resin container of the present invention.

Figure 4:
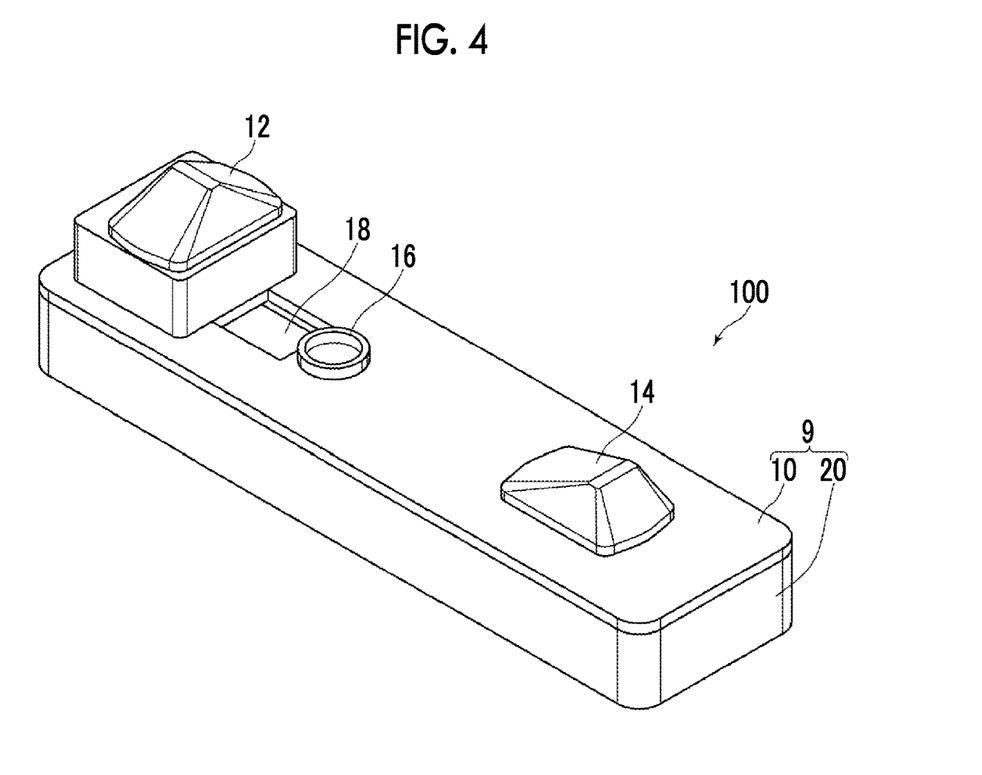
FIG. 4 is a schematic perspective view of an immunochromatographic kit manufactured by a method for manufacturing a resin container.

First, a schematic configuration of an immunochromatographic kit will be described. FIG. 4 is a perspective view of an immunochromatographic kit 100 of one embodiment, and FIG. 5 is an exploded perspective view thereof.

Figure 5:
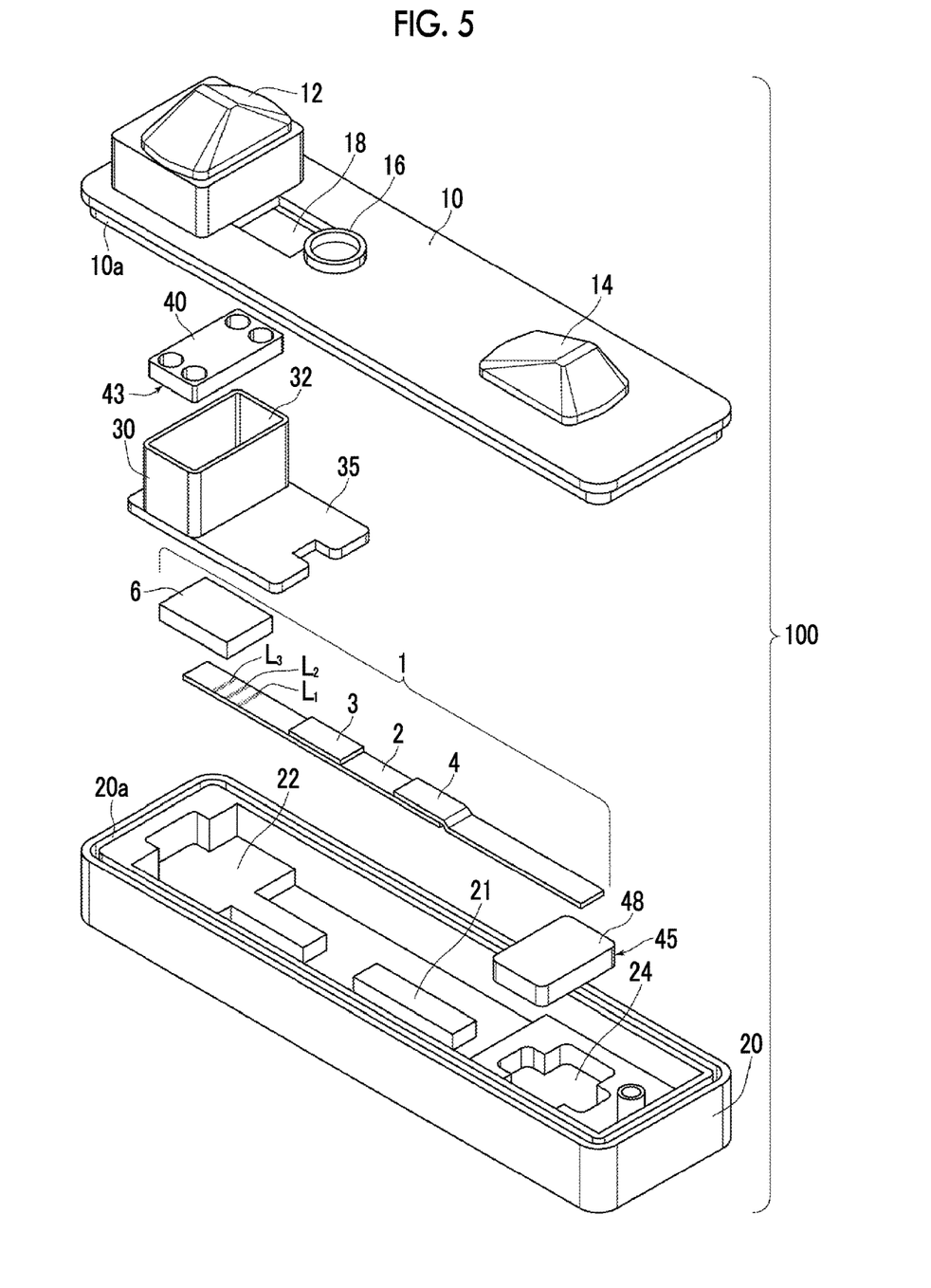
FIG. 5 is an exploded schematic perspective view of an immunochromatographic kit.

As illustrated in FIG. 4 and FIG. 5, in the immunochromatographic kit 100, a housing case 9 includes an inspection strip 1 that has an insoluble carrier 2 having an inspection region of a test substance to spread a specimen liquid, and a first pot 40 and a second pot 45 which include a surface having a sheet member and in which a first amplification liquid and a second amplification liquid are sealed, respectively, in order to amplify a detection signal in the inspection region. The housing case 9 includes a lower case 20 having accommodation portions 21 and 22 in which the inspection strip 1 is disposed, an upper case 10 joined to the lower case 20 along a peripheral edge, and a middle member 30 disposed between the upper case 10 and the lower case 20. In explaining the immunochromatographic kit, the upper case 10 side is defined as an upper part and the lower case 20 side is defined as a lower part.

The middle member 30 has a first pot accommodation portion 32 which accommodates the first pot 40 and includes on the bottom surface an amplification liquid-filling hole for adding the first amplification liquid dropwise onto the insoluble carrier 2. In addition, a protrusive tearing portion that tears up a sheet member 43 is provided at a location facing the sheet member 43 of the first pot 40 in the first pot accommodation portion 32.

In addition, the middle member 30 includes a flow path-forming member 35 extending from a bottom surface of the first pot accommodation portion 32 in the upstream side of the first pot accommodation portion 32. The flow path-forming member 35 is disposed to correspond with the positions above an inspection region $L_1$, a confirmation region $L_2$, and an amplification label region $L_3$, which are to be described later, and is formed of a transparent material so that these regions $L_1$ to $L_3$ can be visually checked.

The upper case 10 includes, on a part facing the first pot 40, a first protrusive deforming portion 12 that is deformed towards the first pot 40 side by being applied with a pressing force from the outside so as to allow the tearing portion of the middle member 30 to tear up the sheet member 43 of the first pot 40. In addition, the upper case 10 includes, on a part facing the second pot 45, a second protrusive deforming portion 14 that is deformed towards the second pot 45 side by being applied with a pressing force from the outside so that a sheet member 48 of the second pot 45 is torn up.

In addition, a hole 16 for dropwise addition of specimen liquid is provided in the upper case 10, the specimen liquid is added dropwise onto a label-holding pad 3 of the inspection strip 1 from this hole 16. In a case where the location of the label-holding pad 3 is adjusted so that the locations of the hole 16 and the label-holding pad 3 correspond to each other, it becomes possible to reliably spot the specimen liquid onto the label-holding pad 3. In addition, the upper case 10 includes an observation window 18 for visually checking the three regions $L_1$ to $L_3$ at positions corresponding to the flow path-forming member 35 of the middle member 30.

In the lower case 20, as an accommodation portion in which the inspection strip 1 is disposed, the insoluble carrier accommodation portion 21 in which the insoluble carrier 2 is mounted is provided, and an absorption pad accommodation portion 22 in which an absorption pad 6 is mounted is provided on the downstream side of the insoluble carrier accommodation portion. In addition, a second pot accommodation portion 24 in which the second pot 45 is accommodated is provided on the upstream side of the insoluble carrier accommodation portion 21.

The inspection strip 1 includes the insoluble carrier 2 spreading specimen liquid, a label-holding pad 3 including a label substance modified with a first substance bondable to a test substance fixed on the insoluble carrier 2, a liquid-sending pad 4 for sending, to the insoluble carrier 2, the second amplification liquid accommodated in the second pot 45 disposed in contact with one end of the insoluble carrier 2, and an absorption pad 6 disposed in contact with the other end of the insoluble carrier 2. The insoluble carrier 2 is fixed to and supported by a back pressure-sensitive adhesion sheet. In addition, the insoluble carrier 2 sequentially has the inspection region $L_1$ including a second substance being bonded to the test substance, the confirmation region $L_2$ including a substance bondable to the first substance, and the amplification label region $L_3$ including a substance being reacted with the second amplification liquid from the label-holding pad 3 side between the label-holding pad 3 and the absorption pad 6.

The first protrusive deforming portion 12 of the upper case 10 is constituted so as to be pressed downward by being pressed down with a finger or the like. Specifically, a protrusion portion is provided on a side facing the first pot 40 of the first protrusive deforming portion 12. The first protrusive deforming portion 12 is deformed and protrude downward (in a concave shape in a case of being seen from the outside) so that the protrusion portion comes into contact with the first pot 40 so as to move the first pot 40 towards the tearing portion to a position where the sheet member 43 of the first pot 40 is torn up by the tearing portion in the first pot accommodation portion 32 of the middle member 30. Therefore, tearing portion tears through the sheet member 43 of the first pot 40, and it becomes possible to supply the first amplification liquid to the outside. The first amplification liquid is added dropwise to the upper portion of the insoluble carrier 2 from the amplification liquid-filling hole that is provided on the bottom surface of the first pot accommodation portion 32 in the middle member 30, and it becomes possible to supply the first amplification liquid to the inspection region $L_1$, the confirmation region $L_2$, and the amplification label region $L_3$ on the insoluble carrier.

As a method for amplifying the signals of metal-based label substances such as metal colloids, it is preferable to use a method in which silver ions and a reducing agent for the silver ions are brought into contact with a label substance, the silver ions are reduced by the reducing agent so as to generate silver particles, and the silver particles deposit on the label substance using the label substance as a nucleus, thereby amplifying signals using the label substance (hereinafter, silver amplification).

In order to realize the silver amplification, a solution containing silver ions may be used as the first amplification liquid, and a reducing agent solution containing a reducing agent for silver ions may be used as the second amplification liquid.

The first protrusive deforming portion 12 is easily deformed by being pushed with a finger or the like, and the first protrusive deforming portion 12 becomes downwardly a protrusion shape (concave shape). A configuration in which the concave shape does not return after this pressing and thus it is possible to maintain the state in which the first pot 40 is pressed, is preferable. The first protrusive deforming portion 12 is configured to press a top portion of a mountain shape, but similarly, the deformation is also possible by pressing the inclined surface of the mountain shape due to the elasticity thereof.

The second protrusive deforming portion 14 is applied with a pressing force, and therefore the sheet member 48 of the second pot 45 is torn up. A protrusion portion is provided on a side facing the second pot 45 of the second protrusive deforming portion 14. The second protrusive deforming portion 14 is applied with a pressing force so that the second protrusive deforming portion 14 protrudes toward the second pot 45 side, that is, so as to be deformed into a concave shape in a case of being seen from the outside, and the protrusion portion comes into contact with a surface of the liquid-sending pad 4 so that the sheet member 48 of the second pot 45 is torn up through the liquid-sending pad 4 is pressed into the second pot 45.

By this operation, the liquid-sending pad 4 is immersed into the second amplification liquid in the second pot 45, and the second amplification liquid can permeate through the liquid-sending pad 4 by capillarity so as to be supplied to the insoluble carrier 2.

The second protrusive deforming portion 14 also is easily deformed by being pushed with a finger or the like so as to become a concave shape. A configuration in which the concave shape does not return after this pressing and thus it is possible to maintain the state in which the second pot 45 is pressed into the liquid-sending pad 4, is preferable.

The immunochromatographic kit 100 of the present invention is to realize highly sensitive analysis by deforming the first and second protrusive deforming portions and supplying the amplification liquid without using a device connected to a power source, and therefore in one embodiment, an aspect in which the deformation is performed by a person's hand is presumed. Therefore, a design in which the amplification liquid such as a solution containing silver ions for silver amplification and a reducing agent liquid containing a reducing agent for silver ions, does not leak to the outside by mistake is preferable, and it is preferable that the first and second protrusive deforming portions 12 and 14 provided in the upper case 10 are provided in an integrated form so as not to have a gap between the other portions of the upper case 10. It is preferable that the protrusive deforming portions 12 and 14 are produced with an extendable material so as to be joined with the other portions of the upper case 10 in a sealed state. The first and second protrusive deforming portions 12 and 14 and the other portions of the upper case 10 may be separately produced and then joined to each other, it is preferable that by injection molding, as a part of the upper case 10, the first and second protrusive deforming portions 12 and 14 are integrally molded as a single continuous member having no joining part.

It is necessary that the protrusive deforming portions 12 and 14 described above have flexibility at which the deformation can be easily performed by a human finger or the like. A modulus of elasticity in bending of a material constituting the protrusive deforming portions is preferably 50 MPa to 350 MPa, and more preferably 70 MPa to 150 MPa.

In addition, in a case where the upper case 10 and the lower case 20 are merely fitted to each other in a case of combining the upper case 10 and the lower case 20, there is a case where the liquid leaks from the gap, and therefore it is preferable that fitting portions of the upper case 10 and the lower case 20 are also bonded in a sealed state. As a method for bonding the upper case 10 and the lower case 20, it is possible to apply the ultrasonic welding method of the present invention.

In general, it is known that ultrasonic welding is difficult to weld unless members to be welded are made of the same material, and the combination of the upper case and the lower case is preferably polyethylene/polyethylene, polypropylene/polypropylene, or ABS (acrylonitrile-butadiene-styrene copolymer)/ABS.

In a case where the protrusive deforming portions 12 and 14 are integrally formed so as not to have contact portions with the other portions of the upper case 10, it is necessary that a material of the upper case 10 has flexibility. On the other hand, the lower case 20 is preferably rigid so as to fix the inspection strip 1 and the second pot 45. Specifically, a modulus of elasticity in bending of a material constituting the upper case 10 is preferably 50 MPa to 350 MPa, and more preferably 70 MPa to 150 MPa. The material constituting the lower case 20 may have a modulus of elasticity in bending of 500 MPa or more, preferably 500 MPa to 900 MPa, and particularly preferably 650 MPa to 750 MPa.

The modulus of elasticity in bending is a value calculated from Equation (1) as follows in an environment of a temperature of 20° C. according to a measurement method of the ISO 178 standard.

In regard to the material for measuring the modulus of elasticity in bending, a test piece in the form of a plate having a width b (mm) and a thickness h (mm) is prepared and the test piece is supported by two fulcrum points with a distance between the fulcrum points set to L (mm). A load of F (N) is applied to a center between the fulcrum points and a degree of deflection (mm) is measured in a direction in which the load is applied. A deflection-load curve is created with deflection S (mm) on a horizontal axis and load F (N) on a vertical axis. A tangent line at the origin point of this curve is obtained, an inclination (($\Delta F/\Delta S$) in a case where an amount of change in load $\Delta F$ (N) and an amount of change in deflection $\Delta S$ (mm)) is calculated, and therefore a modulus of elasticity in bending E (MPa) can be calculated using the following equation.

Modulus of elasticity in bending $E=(L^3/(4bh^3))\times(\Delta F/\Delta S)$ Equation (1)

Accordingly, the combination of materials constituting the upper case 10 and the lower case 20 is most preferably polypropylene/polypropylene containing a softening agent. The softening agent to be used for the polypropylene containing a softening agent is preferably an olefinic elastomer, and a concentration of the olefinic elastomer with respect to the polypropylene is preferably 20% by mass to 60% by mass and particularly preferably 40% by mass to 55% by mass. Specific examples of the softening agent include TAFTHREN (registered trademark) manufactured by Sumitomo Chemical Co., Ltd.

The immunochromatographic kit 100 as described above is prepared as follows.

The insoluble carrier 2 and the absorption pad 6 of the inspection strip 1 are fixed to the insoluble carrier accommodation portion 21 and the absorption pad accommodation portion 22 of the lower case 20. Next, the second pot 45 is attached to the second pot accommodation portion 24 of the lower case 20 with the sheet member 48 facing upward, and the first pot 40 is attached to the first pot accommodation portion 32 of the middle member 30 with the sheet member 43 facing downward. Next, the upper case 10 and the lower case 20 are fitted to each other such that the weld portions 10a and 20a on the outer circumference come into contact with each other.

The jig 60 of the ultrasonic welding device 50 is set in a state where the upper case 10 and the lower case 20 are fitted to each other. The jig 60 used here is configured of the metal jig main body 62 having the concave portion 62a for receiving the lower case 20, and the elastomer 64 disposed on the concave portion 62a. The ultrasonic welding is performed in a state where the bottom surface of the lower case 20 is set so as to come into contact with the elastomer 64 of the concave portion 62a. By sandwiching the two cases 10 and 20 with the horn 58 and the jig 60 and applying ultrasonic vibration to the upper case 10 via the horn 58 while applying pressure, the weld portions 10a and 20a of the upper case 10 and the lower case 20 are welded. As described above, it is possible to produce the immunochromatographic kit 100 in which the outer circumferences of the cases are uniformly welded in a favorable sealed condition, and leakage of the amplification liquid or the like does not occur.

In a case where the upper case 10 is made of a resin containing a softening agent and the lower case 20 is made of a rigid resin like the above-described immunochromatographic kit 100, in the ultrasonic welding method of the related art using a jig in which entire body including the support surface is formed of metal, it is difficult to sufficiently air-tightly join the joining portions between the upper case 10 and the lower case 20. In particular, it was generally difficult to weld uniformly and accurately over the entire welding length exceeding a total length of 40 mm.

The immunochromatographic kit 100 shown in FIG. 4 has a size of 108 mm in a longitudinal direction and 30 mm in a lateral direction, has a total length of about 270 mm, and has a welding length exceeding 40 mm as described above, and therefore in the ultrasonic welding of the related art, sufficient airtightness of the joining portions may not be obtained in some cases. In addition, polypropylene or the like having high chemical resistance as a container used in an immunochromatographic method using silver amplification to realize high sensitivity, or the like, is a material that is difficult to find an optimum condition for ultrasonic welding.

On the contrary, by using the jig 60 having the elastomer 64 on the support surface 60a of the second resin member like the ultrasonic welding method of the present invention, ultrasonic welding with high airtightness can be realized.

EXAMPLES

The upper case and the lower case of the immunochromatographic kit shown in FIGS. 4 and 5 were molded using polypropylene as a material by a general injection molding method. Thereafter, peripheral edges (portions to be welded to each other) of an upper case (first resin member) and a lower case (second resin member) were subjected to ultrasonic welding by a method of the following examples and comparative examples.

As a welding device, an ultrasonic welding machine (power supply part; 2000Xdt 20: 1.25, 20 kHz, actuator part: 2000X aed2.5 stand) of Emerson Japan, Ltd. was used. An aluminum horn and a jig designed exclusively for the upper case and the lower case were used. The weld portions of the upper and lower cases were fitted to each other in advance and set on the lower receiving jig by hand. After the completion of the setting, once a start switch of the ultrasonic welding machine was pushed, ultrasonic waves were applied so as to perform welding under conditions set in advance in a state where the horn was pressed and came into contact with the upper case so as to apply a predetermined pressing force to the upper case. An application time of the ultrasonic wave was 0.5 seconds. After the completion of welding, the horn was raised upward and returned to the initial position so to complete the welding operation. Thereafter, the case which was welded and integrated was taken out by hand.

Examples 1 to 15

As a jig, a jig in which a main body is made of metal (stainless steel: SUS) and a support surface supporting the lower case is made of an elastomer, was used. A material of the elastomer constituting the support surface of each example and a Shore A hardness, a pressing force and an ultrasonic output which are ultrasonic welding conditions, are as shown in Table 1 below. Each thickness of the elastomers was 1 mm.

In the elastomer used in the examples, a Shore A hardness and a modulus of elasticity (Young's modulus) of silicone rubber and a Shore A hardness and a modulus of elasticity of nitrile rubber are shown separately in Table 2. Measurement of the modulus of elasticity was performed according to ISO 527 standard.

Comparative Examples 1 to 15

As a jig, a jig in which a main body part and a support surface supporting a lower case were all made of metal (stainless steel: SUS) was used. A pressing force and an ultrasonic output which are the ultrasonic welding conditions in each comparative example were as shown in Table 1 below.

In each example and comparative example, ultrasonic welding of the upper case and the lower case was carried out five times, respectively, under the same conditions so as to produce five cases (resin containers).

(Evaluation Method of Airtightness)

A negative pressure of −60 kPa was applied to the inside of the housing case from a hole for dropwise addition of specimen liquid of the upper case by using a newly produced negative pressure applying device, and a change in pressure from a negative pressure of −60 kPa at a point where 30 seconds have elapsed after the completion of the application of negative pressure, was measured as pressure fluctuation. The same measurements were carried out for each of the five cases produced under the conditions of the respective examples, and the individual cases were evaluated as follows.

In a case where a pressure fluctuation is within 50 kPa, airtightness is good.

In a case where a pressure fluctuation exceeds 50 kPa and 100 kPa or less, it is an allowable range and airtightness is possible.

In a case where a pressure fluctuation exceeds 100 kPa, it is not acceptable, and airtightness is bad.

Each example and comparative example were evaluated as follows based on the evaluation results of the five cases and are shown in Table 1 as the airtightness evaluation results.

A: All five cases had good airtightness.

B: Of the five cases, the number of cases having good airtightness was 4 or less, and the remaining cases were all acceptable.

C: 1 to 4 out of the five cases were bad.

D: All five cases were bad.

TABLE 1

| | Jig main body Material | Support surface of jig | | Pressing force [kPa] | Ultrasonic output [%] | Airtightness evaluation result |
| --- | --- | --- | --- | --- | --- | --- |
| | | Material | Shore A hardness | | | |
| Example 1 | SUS | Silicone rubber | A50 | 100 | 80 | A |
| Example 2 | SUS | Silicone rubber | A50 | 100 | 100 | A |
| Example 3 | SUS | Silicone rubber | A50 | 200 | 63 | A |
| Example 4 | SUS | Silicone rubber | A50 | 200 | 80 | A |
| Example 5 | SUS | Silicone rubber | A10 | 200 | 100 | B |
| Example 6 | SUS | Silicone rubber | A50 | 200 | 100 | A |
| Example 7 | SUS | Silicone rubber | A70 | 200 | 100 | A |
| Example 8 | SUS | Silicone rubber | A50 | 300 | 63 | A |
| Example 9 | SUS | Silicone rubber | A50 | 300 | 80 | A |
| Example 10 | SUS | Silicone rubber | A50 | 300 | 100 | A |
| Example 11 | SUS | Nitrile rubber | A10 | 200 | 100 | B |

TABLE 1-continued

| | Jig main body Material | Support surface of jig Material | Shore A hardness | Pressing force [kPa] | Ultrasonic output [%] | Airtightness evaluation result |
|---|---|---|---|---|---|---|
| Example 12 | SUS | Nitrile rubber | A30 | 200 | 100 | A |
| Example 13 | SUS | Nitrile rubber | A50 | 200 | 100 | A |
| Example 14 | SUS | Nitrile rubber | A70 | 200 | 100 | A |
| Example 15 | SUS | Nitrile rubber | A90 | 200 | 100 | B |
| Comparative Example 1 | SUS | SUS | — | 200 | 63 | D |
| Comparative Example 2 | SUS | SUS | — | 200 | 80 | D |
| Comparative Example 3 | SUS | SUS | — | 200 | 100 | C |
| Comparative Example 4 | SUS | SUS | — | 300 | 80 | D |
| Comparative Example 5 | SUS | SUS | — | 300 | 100 | C |

TABLE 2

| Elastomer material | Shore A hardness | Modulus of elasticity [MPa] |
|---|---|---|
| Silicone rubber | A10 | 2.5 |
| | A30 | 5.5 |
| | A50 | 15 |
| | A70 | 41 |
| Nitrile rubber | A10 | 1.5 |
| | A50 | 2.5 |
| | A70 | 6.5 |
| | A90 | 15.5 |

Figure 6:
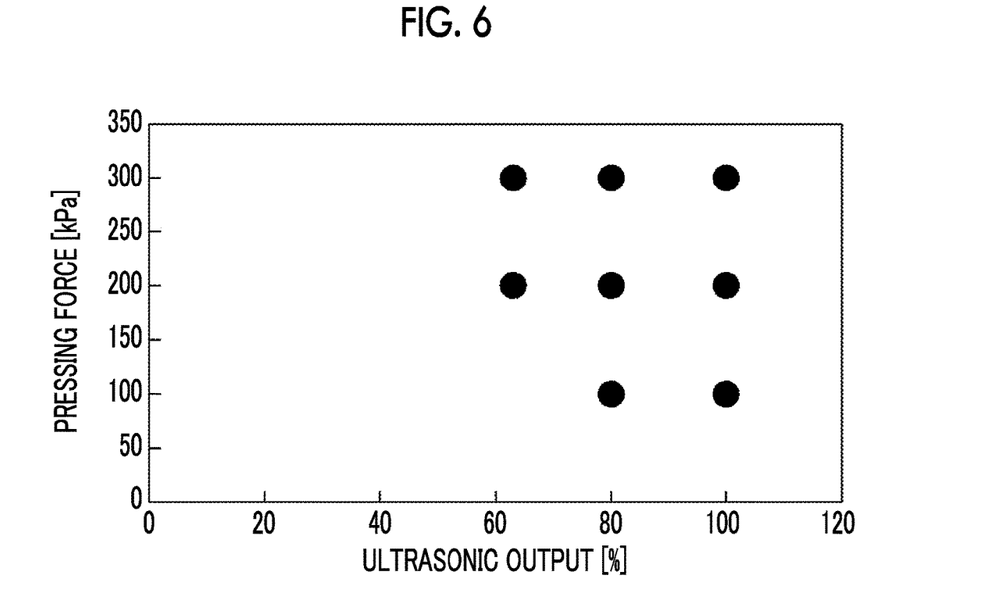
FIG. 6 is a graph illustrating evaluation results of examples.
Figure 7:
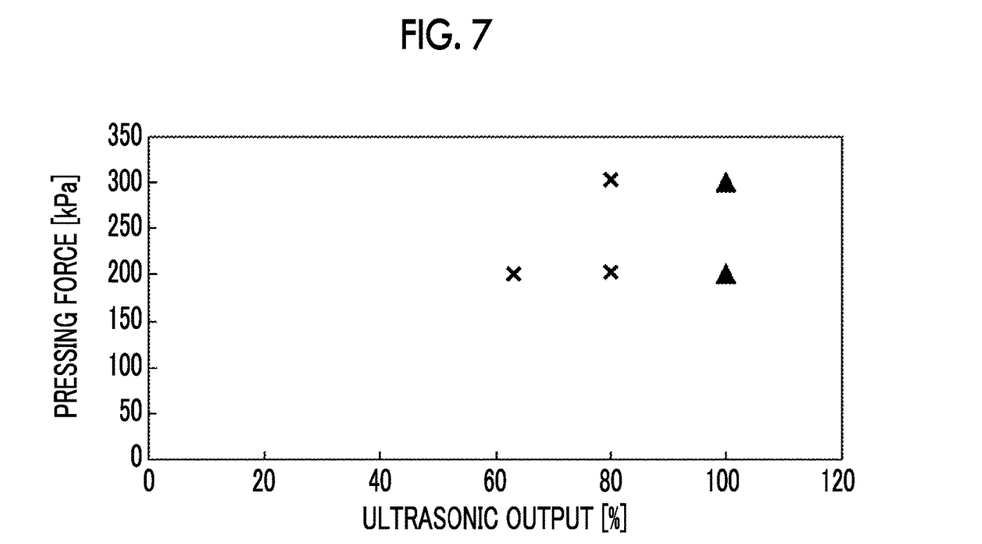
FIG. 7 is a graph illustrating evaluation results of comparative examples.

In FIG. 6, the evaluation results of Examples 1 to 4, 6, and 8 to 10 in which a silicone rubber having a Shore A hardness of A50 was used are plotted in a graph in which a horizontal axis represents the ultrasonic output and a vertical axis represents the pressing force. In FIG. 7, the evaluation results of Comparative Examples 1 to 5 are plotted in a graph in which a horizontal axis represents the ultrasonic output and a vertical axis represents the pressing force. In FIGS. 6 and 7, the airtightness evaluation A is indicated by a black circle (●), the evaluation C is indicated by a black triangle (▲), and the evaluation D is indicated by a cross (x).

As shown in Table 1 and FIG. 7, it was impossible to ensure good airtightness in a case of using the jig in which a metal material was also used to form the support surface, as in Comparative Examples 1 to 5. On the other hand, as in Examples 1 to 15 of the present invention, in a case where an elastomer such as silicone rubber or nitrile rubber was used to form the support surface of the weld object, good airtightness of the joining portions could be maintained. Based on Examples 1 to 15 in Table 1, even in a case where the pressing force was applied to the upper and lower devices while being changed between 100 kPa and 300 kPa and while changing the ultrasonic output between 63% and 100%, the pressure fluctuation was 100 Pa or less in all the samples, and good airtightness was confirmed, and therefore the effect of the present invention was confirmed. Furthermore, in the case where silicone rubber or nitrile rubber, which is an elastomer, is used to form the support surface of the jig, the pressure fluctuation was maintained to 100 Pa or less, but samples showing pressure fluctuations between 50 Pa and 100 Pa increased in the case where the Shore A hardness of the silicone rubber or the nitrile rubber, which is an elastomer, was set to A20 or less. Even in a case where the hardness was set to A80 or more, the pressure fluctuation was 100 Pa or less, but an increase in the samples between 50 Pa and 100 Pa was observed. It was confirmed that it is more preferable to use the elastomer in which a Shore A hardness of silicone rubber is A20 to A80. In particular, as shown in FIG. 7, in a case where silicone rubber having a Shore A hardness of A50 was used as the elastomer, good results were obtained even in a case where the ultrasonic output and the pressing force were changed.

EXPLANATION OF REFERENCES

1: inspection strip
2: insoluble carrier
3: label-holding pad
4: liquid-sending pad
6: absorption pad
9: housing case
10: upper case
10a: peripheral weld portion of upper case
12: first protrusive deforming portion
14: second protrusive deforming portion
16: hole for dropwise addition of specimen liquid
18: observation window
20: lower case
20a: peripheral weld portion of lower case
21: insoluble carrier accommodation portion
22: absorption pad accommodation portion
24: second pot accommodation portion
30: middle member
32: first pot accommodation portion
35: flow path-forming member
40: first pot for first amplification liquid
43: sheet member
45: second pot for second amplification liquid
48: sheet member
50: ultrasonic welding device
52: ultrasonic oscillator
53: connection cable
54: ultrasonic oscillator
56: converter
58: horn
60: jig 60a: support surface
62: jig main body
62a: concave portion receiving second resin member
64: elastomer
70: resin container
71: first resin member
71a: weld portion
72: second resin member
72a: weld portion
100: immunocluomatographic kit

What is claimed is:

1. A method of manufacturing an immunochromatographic kit, the method comprising:
   disposing a pot, in which an amplification liquid is accommodated, and an inspection strip at a predetermined accommodation portion of a lower case;
   contacting and fitting weld portions of an upper case, which configures a housing case together with the lower case, and the lower case with each other;
   setting the lower case and the upper case, which have been fitted with each other, at a support surface of a jig whose support surface is an elastomer, so that the lower case contacts the support surface; and
   welding the weld portions of the upper case and the lower case to each other by sandwiching the upper case and the lower case with the jig and a horn that is disposed facing the jig and applying ultrasonic vibration to the upper case via the horn while applying pressure;
   to thereby manufacture an immunochromatographic kit in which the pot, in which the amplification liquid is accommodated, and the inspection strip are accommodated in the housing case.

2. The method of manufacturing an immunochromatographic kit according to claim 1,
   wherein the jig is made of a metal body and the elastomer.

3. The method of manufacturing an immunochromatographic kit according to claim 1,
   wherein a Shore A hardness of the elastomer is A20 to A80.

4. The method of manufacturing an immunochromatographic kit according to claim 2,
   wherein a Shore A hardness of the elastomer is A20 to A80.

5. The method of manufacturing an immunochromatographic kit according to claim 1,
   wherein Young's modulus of the elastomer is 1 MPa to 60 MPa.

6. The method of manufacturing an immunochromatographic kit according to claim 2,
   wherein Young's modulus of the elastomer is 1 MPa to 60 MPa.

7. The method of manufacturing an immunochromatographic kit according to claim 1,
   wherein the elastomer is made of silicone rubber, nitrile rubber, or butadiene rubber.

8. The method of manufacturing an immunochromatographic kit according to claim 2,
   wherein the elastomer is made of silicone rubber, nitrile rubber, or butadiene rubber.

9. The method of manufacturing an immunochromatographic kit according to claim 1,
   wherein a pressing force of the pressure application is 100 kPa to 300 kPa.

10. The method of manufacturing an immunochromatographic kit according to claim 2,
    wherein a pressing force of the pressure application is 100 kPa to 300 kPa.

11. The method of manufacturing an immunochromatographic kit according to claim 1,
    wherein the upper case and the lower case are made of an olefin resin.

12. The method of manufacturing an immunochromatographic kit according to claim 2,
    wherein the upper case and the lower case are made of an olefin resin.

13. The method of manufacturing an immunochromatographic kit according to claim 11,
    wherein the upper case is made of an olefin resin containing a softening agent.

14. The method of manufacturing an immunochromatographic kit according to claim 12,
    wherein the upper case is made of an olefin resin containing a softening agent.

* * * * *